United States Patent
Matsumoto et al.

(10) Patent No.: US 6,589,492 B2
(45) Date of Patent: Jul. 8, 2003

(54) PROCESS FOR RECOVERING CATALYST COMPONENTS FROM A MOTHER LIQUOR OF LIQUID PHASE OXIDATION

(75) Inventors: Masami Matsumoto, Okayama-ken (JP); Hideaki Fujita, Okayama-ken (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 47 days.

(21) Appl. No.: 09/874,118

(22) Filed: Jun. 6, 2001

(65) Prior Publication Data

US 2002/0016500 A1 Feb. 7, 2002

(30) Foreign Application Priority Data

Jun. 27, 2000 (JP) .................................. 2000-193308

(51) Int. Cl.$^7$ .................. C22B 47/00; C22B 23/00; C01B 7/07
(52) U.S. Cl. ................... 423/49; 423/139; 423/488
(58) Field of Search .................. 423/49, 139, 488; 502/25; 562/414

(56) References Cited

U.S. PATENT DOCUMENTS

| | | | | |
|---|---|---|---|---|
| 3,959,449 A | * | 5/1976 | Shigeyasu et al. | 423/658.5 |
| 4,162,991 A | * | 7/1979 | Jones | 423/139 |
| 4,298,759 A | * | 11/1981 | Harper et al. | 423/49 |
| 5,840,643 A | * | 11/1998 | Park et al. | 502/25 |
| 5,955,394 A | * | 9/1999 | Kelly | 423/49 |

FOREIGN PATENT DOCUMENTS

| | | |
|---|---|---|
| EP | 0902004 | 8/1998 |
| EP | 0999199 | 10/1999 |
| JP | 53 104590 | 9/1978 |

OTHER PUBLICATIONS

Database WPI Section CH, Week 197904, Derwent Publications Ltd. London GB.

* cited by examiner

Primary Examiner—Steven Bos
(74) Attorney, Agent, or Firm—Antonelli, Terry, Stout & Kraus, LLP

(57) ABSTRACT

A process for recovering components of a catalyst from a mother liquor of liquid phase oxidation in production of aromatic carboxylic acids by liquid phase oxidation of aromatic hydrocarbons having substituents with a gas containing oxygen in a presence of a catalyst comprising cobalt, manganese and bromine in acetic acid or acetic acid containing water as a solvent, which process comprises adding a compound generating an ion of an alkali metal to the mother liquor of liquid phase oxidation obtained after separating crystals of the aromatic carboxylic acid from a reaction fluid of the liquid phase oxidation, bringing the mother liquor containing the compound into contact with an ion exchange resin so that the components of the catalyst are adsorbed to the ion exchange resin and recovering the components of the catalyst comprising cobalt, manganese and bromine ion by passing an elution liquid through the ion exchange resin.

By adding the compound generating an ion of an alkali metal to the mother liquor supplied to an ion exchange resin column, contamination of the recovered components of the catalyst with eluted metal ions such as iron can be suppressed and an increase in the concentration of the eluted metal ions in the mother liquor of the oxidation can be prevented. Therefore, the amount of the recycled mother liquor can be increased and the recovery of the catalyst components can also be increased.

7 Claims, 1 Drawing Sheet

PROCESS FOR RECOVERING CATALYST COMPONENTS FROM A MOTHER LIQUOR OF LIQUID PHASE OXIDATION

BACKGROUND OF THE INVENTION

1. Field of the Invention

The present invention relates to a process for recovering catalyst components in production of aromatic carboxylic acids by liquid phase oxidation of aromatic hydrocarbons having substituents.

2. Description of the Prior Art

As the process for producing aromatic carboxylic acids, it is widely conducted that an aromatic hydrocarbon having substituents used as the raw material is oxidized in the liquid phase with a gas containing molecular oxygen at a high temperature and a high pressure in acetic acid as the solvent in the presence of a catalyst such as cobalt and manganese and a bromine compound.

A mother liquor obtained after separating crystals of the aromatic carboxylic acid from the reaction fluid of the liquid phase oxidation by filtration or centrifugal separation (this mother liquor will be referred to as the mother liquor of liquid phase oxidation, hereinafter) contains useful components of the catalyst such as cobalt, manganese and bromine. It is desired that these components are efficiently reused.

However, the mother liquor of liquid phase oxidation contains not only acetic acid used as the solvent and the components of the catalyst but also water as the byproduct of the reaction and intermediate products of the reaction. Moreover, the apparatus used for the reaction is gradually corroded due to corrosive components such as bromine and metal components such as iron, chromium and nickel are eluted into the mother liquor of liquid phase oxidation (the metal components eluted into the mother liquor will be referred to as the eluted metals, hereinafter).

Many of the intermediate products of the reaction and the eluted metals adversely affect the oxidation reaction and cause deterioration in the quality of the product and a decrease in the yield. Therefore, direct recycling and reuse of the mother liquor of liquid phase oxidation is limited.

The components of the catalyst can be recovered from the mother liquor of liquid phase oxidation in accordance with various processes. In one of such processes, for example, a portion of the mother liquor of liquid phase oxidation is concentrated in a concentration tank, organic components in the concentrated product are incinerated and the components of the catalyst are recovered from the residual ashes. In another process, the components of the catalyst are recovered by extracting from the residue in the concentration tank with water as the solvent. In still another process, oxalic acid is added to the mother liquor of liquid phase oxidation so that the metal components are fixed as the salts of oxalic acid and the components of the catalyst are recovered by decomposition of the salts of oxalic acid with the air. The above processes have drawbacks in that a great amount of labor and cost are required.

SUMMARY OF THE INVENTION

As the process for recovering components of the catalyst from a mother liquor of oxidation, processes for recovering the components of the catalyst via adsorption to an ion exchange resin are proposed (Japanese Patent Application Laid-Open Nos. Showa 53(1978)-104590 and Heisei 10(1998)-15390).

In the above process for recovering the components of the catalyst via adsorption to an ion exchange such as the process disclosed in Japanese Patent Application Laid-Open No. Heisei 10(1998)-15390, fine crystals present in the mother liquor of oxidation are removed by filtration using a filter or the like. Then, the components of the catalyst such as cobalt and manganese are converted into bromine complexes using bromine ion present in the clear mother liquor obtained after the filtration and the components of the catalyst are adsorbed to an ion exchange resin in the form of the bromine complexes. The components of the catalyst are recovered by elution with an aqueous solution of acetic acid or water. This process has a drawback in that the liquid obtained by the elution contains eluted metals besides the components of the catalyst and the eluted metals adversely affect the oxidation.

The present invention has an object of providing a process for efficiently recovering components of the catalyst while the amount of eluted metals contained in the recovered components of the catalyst is suppressed in the production of aromatic carboxylic acids by liquid phase oxidation of aromatic hydrocarbons having substituents in the presence of a catalyst comprising cobalt, manganese and bromine ion in a solvent containing acetic acid.

As the result of extensive studies by the present inventors to overcome the above drawbacks, it was found that the amount of the eluted metals can be suppressed by adding a small amount of an ion of an alkali metal to a mother liquor of liquid phase oxidation when cobalt, manganese and bromine are recovered from the mother liquor of liquid phase oxidation. The present invention has been completed based on the knowledge.

The present invention provides a process for recovering components of a catalyst from a mother liquor of liquid phase oxidation in production of aromatic carboxylic acids by liquid phase oxidation of aromatic hydrocarbons having substituents with a gas containing oxygen in a presence of a catalyst comprising cobalt, manganese and bromine in acetic acid or acetic acid containing water as a solvent, which process comprises adding a compound generating an ion of an alkali metal to the mother liquor of liquid phase oxidation obtained after separating crystals of the aromatic carboxylic acid from a reaction fluid of the liquid phase oxidation, bringing the mother liquor containing the compound into contact with an ion exchange resin so that the components of the catalyst are adsorbed to the ion exchange resin and recovering the components of the catalyst comprising cobalt, manganese and bromine ion by passing an elution liquid through the ion exchange resin.

Figure 1:
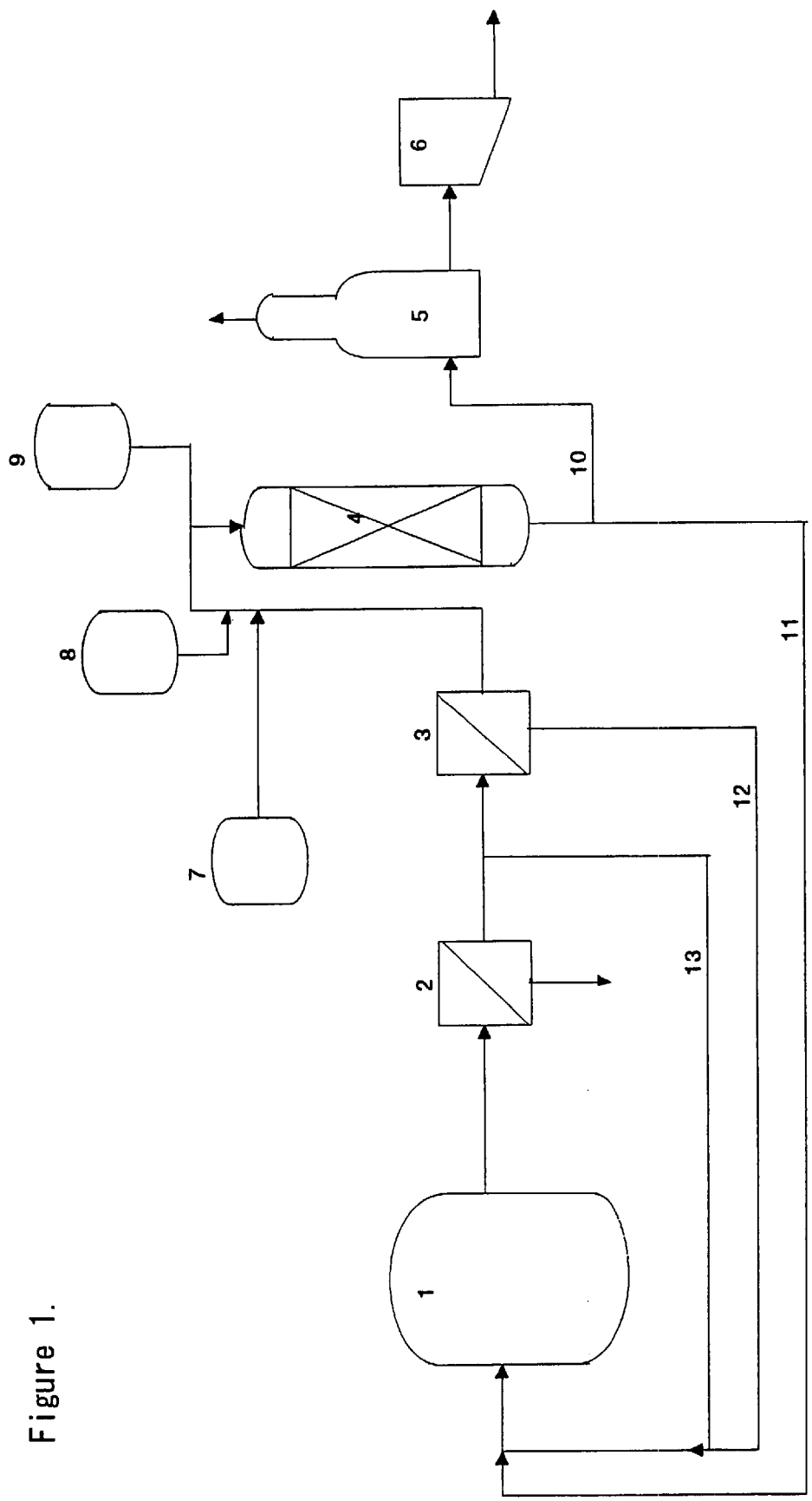
FIG. 1 shows an example of a schematic flow chart of the process for recovering components of a catalyst of the present invention.

The numbers in FIG. 1 have the following meanings: 1: an oxidation reactor; 2: a solid-liquid separator; 3: a high performance filter; 4: an ion exchange resin column; 5: a column for recovery of acetic acid; 6: an incinerator; 7: a tank of an alkali metal; 8: a tank of hydrobromic acid; 9: a tank of an elution liquid; 10: a line for a waste liquid; 11: a line for a liquid containing recovered components of a catalyst; 12: a line for recovered crystals; and 13: a line for recycling a mother liquor of liquid phase oxidation.

DETAILED DESCRIPTION OF THE INVENTION

In the present invention, the raw material used for producing an aromatic carboxylic acid is an aromatic hydrocarbon having substituents. The substituent is oxidized and converted into carboxyl group. Examples of the substituent include methyl group, ethyl group, propyl group, isopropyl group, formyl group and acetyl group. The substituent may be carboxyl group.

As the solvent of the liquid phase oxidation, acetic acid or acetic acid containing water is used. The compounds used for the catalyst are not particularly limited as long as cobalt, manganese and bromine ion are formed in the solvent. As the gas containing oxygen, in general, the air is used. The temperature of the reaction is, in general, in the range of 140 to 240° C. and preferably in the range of 170 to 220° C.

As the ion exchange resin used in the present invention for recovering the components of the catalyst from the mother liquor of liquid phase oxidation, anion exchange resins are preferable. As the anion exchange resin, highly heat resistant anion exchange resins are preferable. Any of anion exchange resins of the strongly basic type and anion exchange resins of the weakly basic type can be used. Anion exchange resins of the weakly basic type have small rates of degradation of the resins although the capacity of adsorption is small and can be advantageously used for preventing rapid degradation. Ion exchange resins, in general, show dimensional changes such as swelling and shrinking depending on the environment of the use. It is preferable that the degree of the dimensional change is small.

Examples of the ion exchange resin used in the present invention include AMBERLITE IRA-400, AMBERLITE IRA-900 and AMBERLITE IRA-96SB (manufactured by ROHM & HAAS Company; trade names); DOWEX 66, DOWEX MSA-1, DOWEX MSA-2, DOWEX SBR-P-C, MONOSPHERE 550A and MONOSPHERE MWA-1 (manufactured by DOW CHEMICAL Company; trade names) and DIAION SA10A, DIAION SA20A and DIAION WA20 (manufactured by MITSUBISHI KAGAKU Co., Ltd.; trade names).

The ion exchange resin is used after being brought into contact with a solution of acetic acid containing bromine ion and converted into the bromide type. To obtain the ion exchange resin of the bromide type, an ion exchange resin is washed with any of water and a solution of acetic acid both containing bromine ion such as sodium bromide and hydrobromic acid and the excess amount of bromine ion is removed by washing with acetic acid or a solution of acetic acid containing 15% or less of water. It is preferable that the acetic acid or the solution of acetic acid contains water in a concentration smaller than that in the mother liquor of liquid phase oxidation.

The mother liquor of liquid phase oxidation is a mixture containing the solvent and small amounts of solid substances such as the aromatic carboxylic acid which is not separated by the separation mechanism, the metals used for the catalyst, unreacted raw materials, intermediates of the reaction and byproducts of the reaction, which are precipitated although the concentrations are smaller than the solubility of each component. When the mother liquor containing solid substances described above as a slurry is supplied to the ion exchange resin, the difference in the pressure within the column increases due to clogging with and accumulation of the solid substances and the continuous operation becomes impossible.

Therefore, it is necessary that the solid substances be removed in advance by filtration of the mother liquor of liquid phase oxidation at a temperature lower than the temperature of operation. The content of the solid substances in the mother liquor of liquid oxidation which is brought into contact with the ion exchange resin (this mother liquor will be referred to as the liquor for treatment, hereinafter) is 0.3% by weight or smaller and preferably 0.05% or smaller.

The concentration of water in the liquor for treatment is 5 to 15% by weight and preferably 8 to 12% by weight. In general, the content of water in the mother liquor of liquid phase oxidation is about 10% and the adjustment of the concentration of water is not necessary before being supplied to the ion exchange resin.

The ratio of the amount by mole of bromine ion to the total amount by mole of cobalt and manganese (this ratio will be referred to as the bromine ratio, hereinafter) in the liquor for treatment is 1.0 or greater and preferably 2.0 or greater. When the liquor for treatment does not satisfy the above condition, it is necessary that bromine such as hydrobromic acid be added. However, when the bromine ratio required for recovery of cobalt, manganese and bromine is satisfied by suitably selecting the conditions of the oxidation, the addition of bromine ion is not required.

The adsorption with the ion exchange resin is conducted at a temperature not exceeding the temperature of heat resistance of the resin and preferably in the range of 30 to 100° C. When the temperature is kept at a temperature in the range of 30 to 100° C. during the adsorption, the ability of adsorbing cobalt, manganese and bromine is remarkably improved from the ability at the ordinary temperature. However, at the same time, the amount of adsorption of eluted metals contained in small amounts also increases.

The ion exchange resin converted into the bromide type as described above is packed into an ion exchange resin column. While the temperature of the ion exchange resin is kept at a temperature in the range of 30 to 100° C., the mother liquor of liquid phase oxidation is passed through the ion exchange resin column and brought into contact with the ion exchange resin. The bromine ratio of the mother liquid may be adjusted in advance, where necessary, By passing the mother liquor of liquid phase oxidation through the ion exchange resin column, cobalt, manganese and bromine which are the components of the catalyst are selectively adsorbed to the ion exchange resin. In this operation, it is inevitable that at least portions of eluted metals contained in small amounts as impurities are also adsorbed to the ion exchange resin.

When small amounts of the eluted metals are mixed into the components of the catalyst which are recycled to the oxidation reactor, the oxidation reaction is adversely affected. Therefore, it is necessary that recycling the eluted metals into the oxidation reactor be prevented as much as possible.

In the present invention, when cobalt, manganese and bromine as the components of the catalyst are recovered from the mother liquor of liquid phase oxidation, a compound generating an ion of an alkali metal is added to the mother liquor of liquid phase oxidation before the mother liquor is passed through the ion exchange resin column. The adsorption of the eluted metals such as iron contained in small amounts is suppressed by the addition of the compound generating an ion of an alkali metal. In other words, the ability to adsorb the eluted metals such as iron is selectively suppressed with the ion of an alkali metal while the ability to adsorb cobalt, manganese and bromine which are the components of the catalyst is not adversely affected.

In the present invention, the type of the ion of alkali metal added to the mother liquor of liquid phase oxidation is not particularly limited as long as a compound generating an ion of an alkali metal is used. It is preferable that a compound generating sodium ion or potassium ion is used. Examples of the compound include sodium hydroxide, potassium hydhoxide, sodium bromide and potassium bromide.

The compound generating an ion of an alkali metal is added in an amount such that the concentration of the ion of an alkali metal is in the range of 10 to 1,000 ppm and preferably in the range of 50 to 400 ppm based on the amount of the mother liquor of liquid phase oxidation. When the concentration exceeds the above range, the recovery of cobalt, manganese and bromine, which is the object of the process, deteriorates. The compound generating an ion of an alkali metal may be added in the solid form or as an aqueous solution.

After the components of the catalyst are adsorbed to the ion exchange resin, the components are recovered by elution with an aqueous solution of acetic acid or water. The content of water in the aqueous solution of acetic acid is 15% by weight or greater and preferably 30% by weight or greater.

The elution may be conducted at a low temperature since the elution can be conducted more easily and sufficiently with a smaller amount of liquid than the amount used in the elution at the same high temperature as that of the adsorption. However, the elution at a low the temperature causes complicated operations and the ion exchange resin may be affected by the change in the environment. Therefore, the elution at a low temperature is not always advantageous.

The ion of an alkali metal is hardly adsorbed to the ion exchange resin in the operation of adsorption and the almost entire amount of the ion of an alkali metal is contained in the liquid obtained by the elution.

Therefore, the undesirable phenomenon that the alkali metal is recovered in combination with the metal components of the catalyst during the elution and recycled to the oxidation reactor does not take place. Therefore, no adverse effects due to contamination of the alkali metal on the oxidation reaction are exhibited.

When the eluted and recovered metal components of the catalyst are recycled to the oxidation reactor and reused, it may occasionally take place that a portion of the ion exchange resin is broken due to troubles in the operation or degradation of the resin and fine powder is formed. The fine powder may then pass through a plate for holding the resin or a filter and goes into the oxidation reactor together with the recovered components of the catalyst. Thus, the fine powder may adversely affects the oxidation or may be mixed into the crystals of the aromatic carboxylic acid. Therefore, it is preferable that a strainer having pores of 10 to 200 $\mu$m is disposed in a line connecting the ion exchange resin column and the oxidation reactor.

After the operation of adsorption is completed, the ion of an alkali metal remaining in the ion exchange resin can be removed by substituting the liquid in the ion exchange resin column with an aqueous solution of acetic acid having a concentration of water smaller that that of the mother liquor of liquid phase oxidation. Alternatively, the alkali metal remaining in the ion exchange resin column may be removed by connecting the outlet of the ion exchange resin column to the line of waste water during a short period of time after the start of the elution so that the liquid in the ion exchange resin column is substituted with the elution liquid.

The process of the present invention will be described specifically with reference to a flow chart. FIG. 1 shows a schematic diagram describing the flow of a mother liquor of liquid phase oxidation generated in an oxidation reactor. A slurry containing a product of oxidation taken out of an oxidation reactor 1 is treated by crystallization and filtered by a solid-liquid separator 2 and the obtained crystals are transferred to a purification system. The major portion of the mother liquor of liquid phase oxidation obtained by the separation is recycled to the oxidation reactor via a line 13. The rest of the mother liquor of liquid phase oxidation is treated by a high performance filter 3 and fine crystals are recovered. The recovered fine crystals are recycled to the oxidation reactor via a line 12. To the clear mother liquor of liquid phase oxidation, hydrobromic acid 8 and an alkali metal 7 are added. The treated mother liquor of liquid phase oxidation is transferred to an ion exchange resin column 4 and the adsorption is conducted. At an outlet of the ion exchange resin column, the mother liquor of liquid phase oxidation containing metals in small concentrations flows out. The mother liquor is then supplied to a column for recovery of acetic acid 5 via a line 10 and acetic acid is recovered. Organic impurities contained in the mother liquor are incinerated in an incinerator 6. An elution liquid 9 is passed through the ion exchange resin column containing the ion exchange resin having adsorbed metals and metal components of the catalyst are recovered by elution. The recovered metal components of the catalyst are recycled to the oxidation reactor via a line 11 and reused.

In accordance with the process of the present invention, in a process for recovering components of the catalyst in which a mother liquor of liquid phase oxidation, which is obtained after separation of crystals from a reaction fluid in the production of an aromatic carboxylic acid by liquid phase oxidation and contains cobalt, manganese and bromine ion which are the components of the catalyst, is brought into contact with an ion exchange resin so that the above components of the catalyst are adsorbed to the ion exchange resin and the adsorbed ions are then recovered by elution with a solution of acetic acid and reused, contamination of the recovered components of the catalyst with eluted metals such as iron can be suppressed by adding a compound generating an ion of an alkali metal to the mother liquor supplied to the ion exchange resin column. The process has the following advantages.

(1) In ordinary process for recovering components of a catalyst, eluted metals such as iron are recovered in combination with the components of the catalyst and adversely affect the oxidation. When the amount of the recycled mother liquor of liquid phase oxidation is increased, the concentration of the eluted metals increases and the oxidation gives a poorer result.

By adding a compound generating an ion of an alkali metal to the mother liquor before being treated by adsorption, adsorption of eluted metals to the ion exchange resin can be suppressed. The amount of the eluted metal mixed into in the mother liquor can be decreased and an increase in the concentration of the eluted metal in the mother liquor of liquid phase oxidation can be prevented. Therefore, in accordance with the process of the present invention, the amount of recycled mother liquor can be increased and a higher recovery of the components of the catalyst can be achieved.

(2) To remove eluted metals which is considered to adversely affect the oxidation, a complicated process has heretofore been conducted. For example, metal components of the catalyst such as cobalt and manganese are first recovered and then eluted metals are removed with a cation exchange resin. In accordance with the process of the present invention, contamination with eluted metals can be prevented without using additional apparatuses other than ordinary apparatuses for recovery of metal components of a catalyst.

Therefore, the components of the catalyst used in the process for producing aromatic carboxylic acids can be easily recovered in accordance with the process of the present invention. Thus, the process of the present invention is important as an industrial process.

EXAMPLES

The present invention will be described more specifically with reference to examples in the following. However, the present invention is not limited to the examples.

In following Examples and Comparative Examples, a glass tube having a jacket and packed with 80 ml of an ion exchange resin of a weakly basic type IRA-96SB (manufactured by ROHM & HAAS Company; a trade name) was used as the ion exchange resin column and was heated and maintained at an elevated temperature. The ion exchange resin was converted into the bromide type by passing 200 ml of a solution of acetic acid containing 10% by weight of hydrobromic acid and hydrobromic acid in the excess amount was removed by passing a solution of acetic acid containing 20% by weight of water. As the elution solution, a solution of acetic acid containing 35% by weight of water was used.

Among the components in a mother liquor of liquid phase oxidation and a recovered liquid, cobalt, manganese, iron and sodium were analyzed in accordance with the atomic absorption spectrometry and bromine was analyzed by titration with silver nitrate.

Examples 1 to 3

Effect of Addition of a Compound Generating an Ion of an Alkali Metal

Into a mother liquor of liquid phase oxidation obtained by liquid phase oxidation of p-xylene using acetic acid containing water as the solvent, sodium hydroxide was added. The resultant solution was supplied to the ion exchange resin column and cobalt, manganese and bromine were recovered.

The composition of the mother liquor of liquid phase oxidation was as follows: water: 9.8%; cobalt: 860 ppm; manganese: 400 ppm; bromine: 2450 ppm; and iron: 5.0 ppm. The rest of the liquor was composed of acetic acid. The bromine ratio was 1.916.

To the above mother liquor of liquid phase oxidation, sodium hydroxide was added in an amount such that the concentration of sodium was in the range of 1,000 to 50 ppm. The liquid for treatment prepared as described above was supplied at an upper portion of the ion exchange resin column heated with hot water at 80° C. and the components of the catalyst were adsorbed to the ion exchange resin. Then, the elution liquid was passed through the column at the same temperature and the components of the catalyst were recovered.

The concentrations of cobalt, manganese, bromine, sodium and iron in the liquid obtained by the elution were measured and the recoveries of the components by the ion exchange resin column were calculated based on the amounts supplied to the column. The results are shown in Table 1.

Comparative Example 1

The same procedures as those conducted in Examples 1 to 3 were conducted except that sodium hydroxide was not added. The result is shown in Table 1.

TABLE 1

|  | Example | | | Comparative |
| --- | --- | --- | --- | --- |
|  | 1 | 2 | 3 | Example 1 |
| Concentration of added Na (ppm) | 1000 | 400 | 50 | 0 |
| Recovery of Co (%) | 99.5 | 99.5 | 99.5 | 99.5 |
| Recovery of Mn (%) | 45.0 | 63.3 | 66.5 | 67.5 |
| Recovery of Br (%) | 93.5 | 95.0 | 95.6 | 97.5 |
| Recovery of Na (%) | 0.0 | 0.0 | 0.0 | not measured |
| Recovery of Fe (%) | 5.5 | 17.5 | 85.0 | 92.5 |

Example 4 to 6

The Effect of the Bromine Ratio

Into a solution of acetic acid containing 10% by weight of water, sources of cobalt, manganese and iron were added in amounts such that the concentrations of cobalt, manganese and iron were the same as those in the mother liquor of liquid phase oxidation used in Examples 1 to 3 and a simulated mother liquor of liquid phase oxidation was prepared. The bromine ratio of the prepared simulated mother liquor was adjusted by adding hydrobromic acid. Then, sodium hydroxide was added in an amount such that the concentration of sodium was 200 ppm. The prepared solution was passed through the ion exchange resin column and the same procedures as those conducted in Examples 1 to 3 were conducted. The results are shown in Table 2.

Comparative Examples 2 to 4

The same procedures as those conducted in Examples 4 to 6 were conducted except that sodium hydroxide was not added. The results are shown in Table 2.

TABLE 2

|  | Example | | | Comparative Example | | |
| --- | --- | --- | --- | --- | --- | --- |
|  | 4 | 5 | 6 | 2 | 3 | 4 |
| Bromine ratio | 2.0 | 1.8 | 1.6 | 2.0 | 1.7 | 1.5 |
| Recovery of Co (%) | 99.5 | 99.0 | 94.4 | 99.5 | 98.5 | 94.2 |
| Recovery of Mn (%) | 67.5 | 40.0 | 22.2 | 67.5 | 30.0 | 17.5 |
| Recovery of Br (%) | 97.5 | 96.8 | 96.1 | 97.5 | 96.9 | 96.5 |
| Recovery of Fe (%) | 35.2 | 15.5 | 7.3 | 92.5 | 68.5 | 28.8 |

What is claimed is:

1. A process for recovering components of a catalyst from a mother liquor of liquid phase oxidation in production of aromatic carboxylic acids by liquid phase oxidation of aromatic hydrocarbons having substituents with a gas containing oxygen in a presence of a catalyst comprising cobalt, manganese and bromine in acetic acid or acetic acid containing water as a solvent, which process comprises the steps of:

(1) adding a compound generating an ion of an alkali metal to the mother liquor of liquid phase oxidation obtained after separating crystals of the aromatic carboxylic acid from a reaction fluid of the liquid phase oxidation, (2) bringing the mother liquor containing the compound generating an ion of an alkali metal into contact with a weakly basic anion exchange resin at 30° to 100° C. so that the components of the catalyst are adsorbed to the anion exchange resin and (3) recovering the components of the catalyst comprising cobalt, manganese and bromine ion by passing an elution liquid through the anion exchange resin.

2. A process according to claim 1, wherein the compound generating an ion of an alkali metal is a compound generating at least one of sodium ion and potassium ion.

3. A process according to claim 1, wherein the elution liquid is water or an aqueous solution of acetic acid containing 15% by weight or more of water.

4. A process according to claim 1, wherein a ratio of an amount by mole of bromine to a total amount by mole of cobalt and manganese in the mother liquor brought into contact with the ion exchange resin is 1.0 or greater.

5. A process according to claim 1, wherein an amount of the compound generating an ion of an alkali metal is in a range of 10 to 1,000 ppm by weight based on an amount of the mother liquor.

6. A process according to claim 1, wherein the anion exchange resin is contained in an anion exchange column and the process further comprises substituting liquid in the anion exchange resin column after step (2) with an aqueous solution of acetic acid having a concentration of water smaller than that of the mother liquor of liquid phase oxidation.

7. A process according to claim 1, wherein step (2) is carried out at a temperature of about 80° C.

* * * * *